United States Patent [19]

Troonen et al.

[11] 4,002,530

[45] Jan. 11, 1977

[54] 6-AMINOPENICILLANIC ACID DERIVATIVE

[75] Inventors: Hugo Troonen, Hoeilaart; Piet Roelants, Watermaal-Bosvoorde; Bernard Boon, Ohain, all of Belgium

[73] Assignee: Recherche et Industrie Therapeutiques (R.I.T.), Belgium

[22] Filed: Jan. 9, 1975

[21] Appl. No.: 539,900

Related U.S. Application Data

[62] Division of Ser. No. 449,180, March 7, 1974, Pat. No. 3,883,511.

[52] U.S. Cl. .............................................. 195/36 P
[51] Int. Cl.[2] ......................................... C12D 9/08
[58] Field of Search ................................. 195/36 P

[56] References Cited

UNITED STATES PATENTS

| | | | |
|---|---|---|---|
| 3,024,168 | 3/1962 | Lein et al. ........................ | 195/36 P |
| 3,093,547 | 6/1963 | Margreiter et al. .............. | 195/36 P |

*Primary Examiner*—Alvin E. Tanenholtz
*Attorney, Agent, or Firm*—Alan D. Lourie; William H. Edgerton

[57] ABSTRACT

Penicillin derivative substituted at the 6 position with a (D)-[(2-amino-2-carboxy)-ethylthio]-acetamido group is obtained from *Acremonium Chrysogenum* new strain ATCC 20 389 or by semi-synthetic route. The product is an antibacterial agent.

3 Claims, No Drawings

6-AMINOPENICILLANIC ACID DERIVATIVE

This is a division of application Ser. No. 449,180, filed Mar. 7, 1974, now U.S. Pat. No. 3,883,511.

The present invention relates to a novel penicillin derivative which is antibiotic RIT D-2214 or 6-(D)-{[(2-amino-2-carboxy)-ethylthio]-acetamido}-penicillanic acid of the formula:

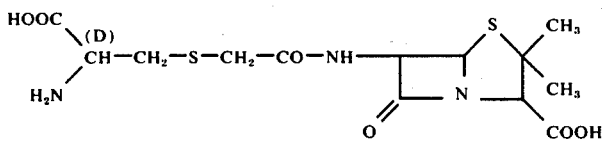

and to a method for the production thereof.

Antibiotic RIT D-2214 is an amphoteric compound susceptible to form salts with pharmaceutically acceptable cations such as sodium, postassium, calcium and ammonium and acids, said salts are preferably mono-salts with cations e.g. the mono-saline, mono-potassium and mono-ammonium salts.

According to this invention, antibiotic RIT D-2214 is produced either by cultivating under controlled conditions a hitherto undescribed strain of *Acremonium chrysogenum* species which has been deposited at the American Type Culture Collection (Rockville, Maryland, U.S.A.) where it received the *Acremonium chrysogenum* ATCC 20 389 designation or by semi-synthetic route.

For producing antibiotic RIT D-2214, the *Acremonium chrysogenum* strain ATCC 20 389 is cultivated in a culture medium containing assimilable sources of carbon, nitrogen, inorganic salts and L-carboxymethyl-cysteine, under submerged aerobic conditions until a substantial amount of said compound is produced by said organism in said culture medium, said culture medium being maintained at a temperature of from approximately 20° C to approximately 37° C and the growth of the organism being carried out for a period of approximately 36 to 96 hrs and the antibiotic RIT D-2214 is recovered from said medium.

*Acremonium chrysogenum* ATCC 20 389 has been obtained by mutagenesis of the *Cephalosporium* sp. BROTZU strain (ATCC 11 550).

We have found that the *Acremonium chrysogenum* ATCC 20 389 strain is auxotrophic for lysin and alphaaminoadipic acid and its fermentation results in the production of a number of antibiotic substances, e.g. penicillin N, Cephalosporin C, Cephalosporin P and/or antibiotic RIT D-2214, depending on the nature of the precursor incorporated to the culture medium.

The characteristics of the *Acremonium chrysogenum* ATCC 20 389 strain are given below and with reference to its parental strain ATCC 11 550 and to the *Cephalosporium chrysogenum* ATCC 14 615 type strain.

The strains were examined for homogeneity and stability of their characters through cultures of 100 single-conidium isolates. The Brotzu strain showed good homogeneity in the colony characters on several culture media, while the ATCC 20 389 mutant revealed some variation in the external pattern of the colonies. The type strain ATCC 14 615 was homogenous in 96 of the 100 single-conidium isolates, the four remaining ones being not pigmented and morphologically distinct.

Each strain was compared by cultures of one mass-conidium and three single-conidium transfers on seven distinct culture media.

The formulae of the culture media are as follows:

MYA4 malt extract 40 g, yeast extract 3 g, agar 20g per liter

MYA2 malt extract 20 g, yeast extract 3 g, agar 20 g per liter

PDA glucose 20 g, potato extract from 200 g pelled potato in water, agar 20 g per liter CZA saccharose 30 g, sodium nitrate 3 g, dipotassium hydrogen orthophosphate 1 g, magnesium sulphate crist. 0.5 g, potassium chloride 0.5 g, ferrous sulphate 0.01 agar 15 g per liter YDPA glucose 20 g, yeast extract 5 g, bactopeptone 10 g, agar 20 g per liter DYAA glucose 10 g, yeast extract 3 g, asparagine 0.5 g, dipotassium hydrogen orthophosphate 1 g, magnesium sulphate crist. 0.5 g, hydrated ferric chloride 0.01 g, agar 25 g per liter WAKS glucose 10 g, beef extract 5 g, bactopeptone 5 g, sodium chloride 5 g, agar 20 g per liter Denotations of color are made by reference to their reference number in Seguy, E. Code Universel des Couleurs, Ed. Lechevalier, Paris, 1936.

Species identification

Both parental and mutant strains exhibit macroscopic and microscopic characters identical to those of the *Cephalosporium chrysogenum* Thirum. and Sukap. type strain and are representing this species.

The generic name *Cephalosporium* having been shown erroneous for the genus (see W. Gams in Cephalosporiumartige Schimmelpilze. Stuttgart 1971), the earliest name *Acremonium* has been adopted and therefore the *Acremonium chrysogenum* designation is proposed for the strain ATCC 20 389.

Description of strain ATCC 20 389

Culture in vitro on malt extract yeast agar at 4% (MYA4).

Colonies, on MYA4, growing slowly and restrictely (8–10 mm after 10 days at 22° C), first white becoming ivory to rose-ivory (paler than S.190), reverse uncolored to pale ochre (S.200) with no pigmentation of the culture medium, round-shaped to angular, margin abrupt and crenate, surface elevated, strongly and densely wrinkled, mahor wrinkles high, radiate, irregularly undulate to sigmoid, sometimes furcate, anastomosed transversely by lower minor wrinkles, thick, becoming larger and convoluted and finally blending together into high mesanteriform massa, crateriform at the center, texture soft becoming ceraceous.

Hyphae mucilaginous, prostrate (aerial only on particular media), regular and cylindrical narrow, 1–2.5 $\mu m$ diam., septate, perpendicularly branched, with smooth and thin hyaline wall, aggregated in prostrate radiate and transverse ropes, often anastomosed with adjacent hyphae by short unseptate anastomoses, breaking down at maturity into separated hyphal cells of various shapes.

Conidiophores: phialides numerous arising solitary, lateral and perpendicular on the prostrate hyphae, erected, more or less undulate, simple, not branched, 25–60 μm length, 1.5–2.5 μm wide at the base, progressively attenuating towards the apex to 1–1.5 μm wide in a cylindrical tube without collarette, always with one basal septum at 2–4(10) μm above the hypha, delimitating a basal cell including an hyphal portion and not differentiated, sometimes with a second septum at 2–10 μm from the basal one, with smooth and thin wall.

Conidia: phialospores produced endogenously and singly at the apex of the phialide, agglutinating into a sphaerical dropplet of mucilage, elliptical or lanceolate, often attenuated and flattened at the base, larger at the lower half, often slightly strangulated at the middle, blunted or slightly pointed at the apical end, often asymmetrical in shape, amygdaliform or planoconvex, straight or slightly curved, with smooth thin mucilaginous wall and often biguttulate contents, of variable length, measuring 2.5–11 × 1.5–3.5 μm, mostly 4–7 × 2–3 μm.

Hyphal cells resulting from the fragmentation of mature hyphae with swellings, thickened walls and gelatinized transverse septa, observed after six weeks, with distinct shapes: (1) linear, straight, cylindrical and (2) vermiform, undulate or contorted, cylindrical, not inflated, 7–10 × 1–2 μm, not numerous; (3) moniliform, simple or furcate, slightly inflated at intervals and the ends, not septate, 10–15 × 2.5 μm, numerous; (4) panduriform fiddle-shaped, first short hyphal cells swollen at both ends, strangulate at the middle, entire or septate, 5–10 × 2–3 μm, becoming larger through unequal or equal swelling of each half into chlamidospore-like cells with thick wall, 5–μm diam., numerous; (5) sphaeropedunculate, developed from the swelling of a single end of an hyphal cell, the other end remaining almost unchanged, swollen end globose, thickwalled, 5–6 μm diam., appendages cylindrical, 1.5–2.5 μm wide, numerous; (6) inflated hyphal cells, intercally or terminal, the swelling involving the entire length of the cell, subglobose to ovate, wall slightly thickened, 3–8 μm, unfrequent.

On most of the used culture media, the strain ATCC shows absence of yellow pigmentation, except a faint yellow tinge on MYA2. Its growth is restricted, submerged and dendroid on PDA and very reduced on CZA, because of the deficiency in lysine.

Comparison between ATCC 20 389 mutant strain and parental strain ATCC 11 550.

The comparison with the parental strain makes possible the diagnostic differentiation of the mutant ATCC 20 389 on the base of the following characters: growth, color of the surface and the reverse of the colony, diffusion of yellow pigment in the culture media, surface pattern of the colony and the micromorphology and frequency of the desintegrated hyphal cells in mature culture.

Some variation in the colony pattern is observed between single-conidium isolates of the ATCC 20 389 mutant, in the enlargment and folding of the wrinkles up to their confluency into mesenteriform massa from the center up to the margin; but is represents different stages of development of a common character.

No significant difference is observed in the shape and size of the conidiophores and conidia between the parental and mutant strains. In both strains also, sporulation occurs on the same culture media as DYAA, YDPA, WAKS and also CZA (if added with lysine for the mutant), and not on MYA4 or PDA.

Comparison between ATCC 20 389 and its parental strain ATCC 11 550 on different culture media, after 6 weeks at 22° C.

1. On MYA4, Malt-yeast-agar 4%.
ATCC 20 389
Growth: 16 mm diam.
Color: white to rose-ivory (paler than S.190), reverse pale ochre (S.200); no pigment.
Surface: wrinkles dense, thick, high, radiating, undulating, anastomosing in the depth, confluent at the center into a high mesenteriform and crateriform massa, also sometimes confluent up to the margin.
Margin high abrupt and crenate.
Hyphal cells moniliform and vermiform up to 2.5 μm wide sphaeropedunculate and panduriform small, thickwalled, inflated up to 6 μm diam.; terminal inflated cells unfrequent up to 8 μm diam.
ATCC 11 550
Growth 20–22 mm diam.
Color: rapidly intense yellow (S.272); reverse orange yellow (S.256); diffusion of intense yellow pigment (S.242)
Surface: wrinkles lower, radiating but zig-zag and furcate, developing a reticulum by anastomose up to the margin, not confluent, with center almost not elevated.
Margin abrupt, crenate.
Hyphal cells linear and vermiform; sphaeropedunculate and panduriform larger, up to 12 μm with thick wall.

2. On MYA2, Malt-yeast-agar 2%
ATCC 20 389
Growth 33 mm diam.
Color: ivory to pale olive yellow (S.264); reverse pale yellowish (S.228); diffusion of yellow pigment none or very fainted.
Surface: wrinkles undulate, radiating from the crateriform elevated center, progressively attenuated to the margin, very pooly anastomosed.
Margin plane, fibrillose, submerged.
Hyphal cells mostly linear, vermiform and panduriform, often septate, 5–15 × 2–3.5 μm; inflated cells up to 5 μm diam. unfrequent.
ATCC 11 550
Growth 40–50 mm diam.
Color pale yellow (S.259–260); reverse deep organe yellow (S.226) diffusion of yellow pigment intense.
Surface wrinkles low, poorly developed from the center, radiate and undulate, more developed at the margin with anastomoses.
Margin extending under the agar.
Hyphal cells, mostly linear, doliform, toruloid, 5–15 × 2–3.5 μm, panduriform septate 8–10 × 3–4 μm, globose or subglobose cells up to 6 μm diam.

3. on PDA, Potato-dextrose-agar.
ATCC 20 389
Growth 20 mm diam.
Color milky, reverse uncolored; diffusion of pigment none.
Surface almost entirely submerged, with local superficial white tufts.

Margin submerged, deeply dendroid.
Hyphal cells, mostly moniliform and panduriform, much enlarged, thick-walled, 10–18 × 4–6 μ; inflated cells intercalary and terminal, elliptical or pyriform, up to 8 μm diam.
ATCC 11 550
Growth 37 mm diam.
Color: intense pure yellow (S.271); reverse dark yellow (S.212); diffusion of yellow pigment intense.
Surface: wrinkled radiately at the center only, plane towards the margin.
Margin outlined finely dendroid.
Hyphal cells linear and monilifrom 5–18 × 1.5–2.5 μm; panduriform irregular, thick walled, 10–14 × 3–5 μm; few globose inflated cells up to 12 μm diam.
4. on CZA, Czapeck agar.
ATCC 20 389
Growth 5–10 mm, very restricted (because of lysine deficiency).
Color milky, no pigment.
Surface submerged.
Margin dendroid.
Hyphae toruloid, 3–5 μm diam., with production of lateral globose cells up to 4 μm diam., and intercalary panduriform cells up to 7 μm diam.
ATCC 11 550
Growth 45–50 mm.
Color: dark yellow (S.258), reverse concolorous; diffusion of yellow pigment intense.
Surface: wrinkles regularly radiating from the center, furcate and attenuate at the margin.
Margin, regular, submerged.
Hyphal cells: regular with some intercalary globose, elliptical, pyriform and panduriform cells, 5–15 × 3–5 μm; some subglobose cels up to 10 μm diam.
5. on YDPA, Yeast-dextrose-peptone-agar.
ATCC 20 389
Growth 30 mm diam.
Color: pale ochre-rose (S.200) to light grey (S.235); reverse amber; no yellow pigment.
Surface: emerged up to 20 mm diam., wrinkles thick, radiate from a center, undulate, bifurcate and attenuate near the margin, not anastomosed.
Margin diffuse, submerged, 5 mm wide.
Hyphal cells: globose inflated cells up to 8 μ diam.; panduriform up to 12 × 4 μm.
ATCC 11 550
Growth 38 mm.
Color: ivory turning pale yellow (S.319); some diffusion of pigment.
Surface: emerged up to 26 mm diam., with wrinkles radiate from not prominent center, sigmoid, attenuate at the margin, not anastomosed.
Margin diffuse, submerged, 5–6 mm wide.
Hyphal cells: globose inflated up to 7 μm diam. or doliform up to 10 × 4 μm, intercalary.
6. on DYAA, dextrose-yeast-asparagin-agar.
ATCC 20389
Growth 25 mm.
Color: rose-ivory (paler than S.200), no yellow pigment.
Surface: emerged up to 15 mm diam., wrinkles fine radiate, straight, attenuate and bifurcate near the margin, not anastomosed.
Margin diffuse, submerged, 5 mm wide.
Hyphal cells: intercalary inflated globose up to 8 μm diam. or elliptical up to 13 × 5 μm.
ATCC 11 550
Growth 38 mm diam.
Color: ivory turning pale yellow (S.259); some diffusion of yellow pigment.
Surface: emerged up to 12 mm diam., with wrinkles low, radiate, no anastomosed.
Margin diffuse, submerged, 13 mm wide.
Hyphal cells: some panduriform 10 × 3 μm; terminal and intercalary inflated globose up to 6 μm diam. or elliptical up to 10 × 5 μm.
7. on WAKS, Waksman's medium.
ATCC 20 389
Growth 25 mm.
Color: rose-ivory (S.250), reverse uncolored; no yellow pigment.
Surface: emerged up to 12 mm diam., wrinkles few, reticulate not radiate, anastomosed and edging the surface.
Margin submerged 6–10 mm.
Hyhal cells: linear; inercalary inflated globose up to 8 μm diam. or elliptical up to 13 × 5 μm; mostly panduriform up to 12 × 4 μm.
ATCC 11 550
Growth 50 mm.
Color: ivory turning pale yellow (S. 319); some diffusion of yellow pigment.
Surface: emerged up to 25 mm diam., wrinkles radiate, sigmoid, attenuate near the margin, not anastomosed.
Margin diffuse submerged, 5 mm wide.
Hyphal cells: terminal and intercalary inflated cells globose up to 7 μm diam. or elliptical up to 10 × 5 μm.

As indicated hereinabove, antibiotic RIT D-2214 is produced by the cultivation of the Acremonium chrysoqenum strain ATCC 20 389. Different culture media may be used for producing antibiotic RIT D-2214 by cultivation of strain ATCC 20 389. The carbon source may be for example dextrose, sucrose, maltose, dextrin, lactose, starch, vegetable oils and other carbon sources known to the art. The nitrogen source may be for example casesin hydrolysates, malt extract, fish meal, soybean meal, peanut meal, meat meal, corn steep liqour, pentones, amino acids or their analoques. As assimilable nitrogen sources ammonium salts such as ammonium acetate, phosphate or sulphate may also be employed. Minor elements necessary for optimum growth and development of the organism used for the production of anitibiotic RIT D-2214 may also be included in the culture medium. Such thrace elements commonly occur as impurities in the other constituents of the medium in amounts sufficient to meet the growth requirement of the organism employed in this invention.

Owing to the auxotrophic nature of the strain ATCC 20 389 it is essential to adequately supplement the medium with L(+) lysine for optimum growth and development of the strain and with L(+) carboxymethylcysteine as a precursor for the production of antibiotic RIT D-2214. Lysine and carboxymethylcysteine are preferably added so as to be present in a concentration of about 0.001 % to 1% weight in volume of the total culture medium and preferably in a concentration of about 0.05 to 0.1%.

The culture medium may also contain those specific nutrients known to the art for improving the production yield of cephalosporin C by a Cephalosporium strain. Thus, the culture medium composition for the production of antibiotic RIT D-2214 may be improved by adding either D, L or DL methionine, L-cysteine, oleic acid, methyl oleate, ammonium sulfate, calcium sulfate or others. Among them, DL-methionine is a particularly valuable nutrient for improving the production yield of antibiotic RIT D-2214. DL-methionine may be supplemented to the medium at a concentration from about 0.01 to 1% (weight/volume), optimally at about 0.2 to 0.5%.

The initial ph of the culture medium can be varied. However, it has been found desirable that the initial pH of the medium be between 6.5 and 7.5. Submerged, aerobic culture conditions are conditions of choice for the production of antibiotic RIT D-2214. FOr preparation of relatively small amounts, shake flasks and surface culture in bottles can be employed but for the preparation of large amounts, submerged aerobic cultrue in sterile tanks is preferred. The medium in the sterile tank can be inoculated with a sporule suspension; but because of the growing lag experienced when a sporulated suspension is used as the inoculum, the vegetative form of the cultrue is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism; and when a young active vegetative inoculum has been obtained, to transfer the vegetative inoculum aseptically to the large tank. The medium in which the vegetative inoculum is produced can be either the same as or different from the medium utilized for the large scale production of antibiotic RIT D-2214.

The organism which produces antibiotic RIT D-2214 does grow over a wide temperature range between 22°–35° C.

Optimal production of antibiotic RIT D-2214 seems to occur at temperature of 22°–30° C. In general, maximum production of the antibiotic occurs within about 3 to 5 days after inoculation of the culture medium.

As is customary in aerobic, submerged culture processes, sterile air is blown through the cultre medium. For efficient growth of the organism and antibiotic RIT D-2214 production, the volume of air employed in the production tank is from 0.25 to 1.5 volume of air per minute per volume of culture.

The preferred volume is 0.5 –1.0 volume of air per minute per volume of culture medium.

The concentration of antibiotic activity in the culture medium can be followed readily during the fermentation period by testing samples of the culture medium for their inhibitory activity against the growth of organisms known to be inhibited by the presence of antibiotic RIT D-2214.

The organism *Alcaligenes viscolactis* has been found particularly usefull for this purpose owing to its very high sensitivity towards antibiotic RIT D-2214 and its lack of sensitivity towards the cephalosporins P group.

The testing of samples can be carried out by the well known agar-diffusion method on Petri dishes or on plates.

The antibiotic activity produced during the fermentation occurs in the antibiotic broth. Accordingly, isolation techniques employed in the production of antibiotic RIT D-2214 are designed to permit maximum recovery of the antibiotic from the broth. Thus, for example, mycelium and undissolved solids are removed from the fermentation broth by conventional means such as filtration or centrifugation, and antibiotic RIT D-2214 can be recovered from the filtered or centrifuged broth by employing extraction or adsorption techniques.

For the recovery of antibiotic RIT D-22214 by adsorption techniques, varous adsorbents and ion exchange resins can be used, for example, carbon, silica gel, alumina, cellulose, ion exchange resins and non-ionic resins. Antibiotic RIT D-2214 can be adsorbed from an aqueous solution onto one of the above or similar adsorbents. The adsorbed antibiotic RIT D-2214 can be eluted from the adsorbent by suitble elution techniques, such as by washing the adsorbent on which the antibiotic RIT D-2214 is adsorbed with solvent. When the elution is carried out by washing the ionic resins on which the antibiotic RIT D-2214 is adsorbed, with a solution of, e.g. ammonium formate, sodium acetate or potassium acetate, the process results in elution of antibiotic RIT D-2214 as the monoammonium, monosodium or monopotassium salt, respectively. When the elution is carried out by washing the non-ionic resins on which the antibiotic RIT D-2214 is adsorbed, the eluent is water.

It has been found that adsorbents previously described as suitable for the adsorption of cephalosporin C and penicillin N, such as weakly and strongly basic resins, for example the Amberlite resins of the IRA-68 and IRA-400 series and analogues as well as non-ionic crosslinked polystyrene polymer resins, for example the Amberlite XAD series or analogues, preferably XAD-2 and XAD-4, are also suitable to adsorb the antibiotic RIT D-2214 from the production broth or from an aqueous solution thereof.

For the recovery of antibiotic RIT D-2214, systems previously described for the extraction of cephalosporin C or penicillin N such as the liquid anionic resins, for example the Amberlite LA series, or extraction into organic solvent after N-acylation of antibiotic RIT D-2214 in solution may be used.

The same techniques as those hereinabove mentionned for the recovery of antibiotic RIT D-2214 from the fermentation broth are also possibly used for its purification, preferably the adsorption technique on weakly or strongly basic resins cr on the non-ionic crosslinked polystyrene polymer resins, for example, the Amberlite XAD series or the like. Antibiotic RIT D-2214 may for example be purified by adsorption of crude antibiotic RIT D-2214 onto a non-ionic resin of the Amberlite XAD series or the like, preferably XAD-4, followed by elution with deionized water.

As indicated hereinabove, antibiotic RIT D-2214 may also be obtained by semi-synthetic route. According to this embodiment, D-cysteine is reacted with a 6-($\alpha$-haloacetamido)-penicillanic acid (preferably in the form of a neutral salt such as the sodium, potassium or the ammonium salt), said 6-($\alpha$-haloacetamido)-penicillanic acid salt being preferably 6-($\alpha$-bromoacetamido-penicillanic acid ammonium salt according to the following scheme:

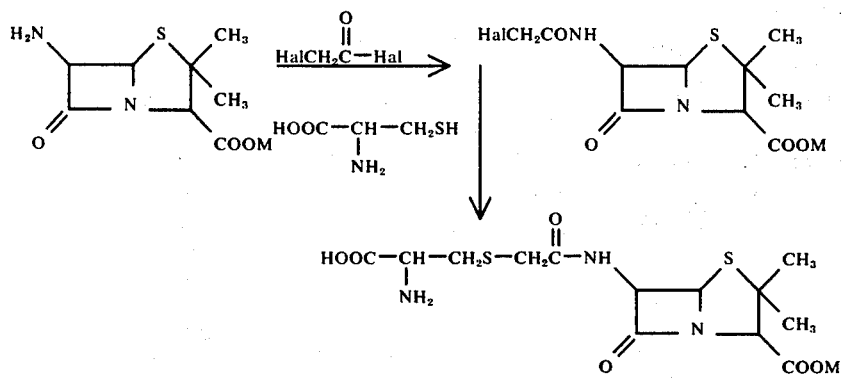

wherein M is hydrogen or a pharmaceutically acceptable nontoxic cation such as sodium, potassium and ammonium; Hal is halogen such as chloro, bromo or iodo.

It is obvious that the semi-synthetic route allows not only the production of the D epimer of antibiotic RIT D-2214 but also the production of the L epimer and of the DL racemic form, when starting from the L- or DL-cysteine respectively.

The reaction is performed in a suitable solvent such as water at a pH comprised between 6 and 9, preferably between 7 and 8 at a temperatuure comprised between 0 and 50° C. preferably between 20 and 30° C, according to L. Michaelis and M.P. Schubert in J. Biol. Chem. 106, 331–41 (1934).

Antibiotic RIT D-2214 exhibits inhibitory activity against the growth of both Gram-positive and Gram-negative bacteria.

Antibiotic RIT D-2214 has been tested in form of the mono ammonium salt in position 3 of the penam nucleus and, for that reason, is herein below charcterized as this monoammonium salt.

The levels at which monoammonium salt of antibiotic RIT D-2214 shows inhibition against the growth of illustrative organisms are set forth in Table 1, as a comparative trial with ampicillin. The inhibitory levels were determined by the broth dilution test. A series of tubes containing varied concentrations of the monoammonium salt of antibiotic RIT D-2214 were inoculated with the test organism to determine the minimum concentration of the ammonium salt of antibiotic RIT D-2214 in mcg/ml. in the broth substrate which inhibited organism growth for a period of about twenty hours at 35° C.

As indicated in Table 1, the monoammonium salt of antibiotic RIT D-2214 exhibits a strong activity against Gram-positive and -negative bacteria. Other salts of antibiotic RIT D-2214, as for example the calcium salt and the potassium salt exhibit similar antibacterial acitivitly.

TABLE 1

| Test organism | Minimum Inhibitory concentration in mcg/ml. | |
|---|---|---|
| | Antib. RIT D-2214 | Ampicillin |
| Corynebacterium xerosis | <0.02 | 0.1 |
| Staphylococcus aureus | 1.25 | 1.25 |
| Staphylococcus aureus Pen.resist. | 80.0 | 20.0 |
| Bacillus subtilis | 0.3 | 0.3 |
| Escherichia coli | 1.25 | 1.25 |
| E. coli Pen. resistant | 80.0 | 80.0 |
| Alcaligenes faecalis | 1.6 | 1.6 |
| Aerobacter aerogenes | 1.25 | 1.25 |

TABLE 1-continued

| Test organism | Minimum Inhibitory concentration in mcg/ml. | |
|---|---|---|
| | Antib. RIT D-2214 | Ampicillin |
| Klebsiella pneumoniae | 80.0 | 40.0 |
| Salmonella paratyphi | 1.25 | 1.25 |
| Salmonella meleagridis | 0.6 | 0.6 |
| Salmonella typhi | 0.6 | 0.6 |
| Salmonella typhimurium | 40.0 | 40.0 |
| Salmonella panama | 40.0 | 2.5 |
| Salmonella anatum | 0.6 | 0.6 |
| Shigella sonnei | 20.0 | 2.5 |
| Proteus mirabilis | 1.25 | 1.25 |
| Proteus morganii | 40.0 | 20.0 |
| Vibrio el tor | 0.6 | 1.25 |
| Brucella abortus | 20.0 | 0.6 |
| Bordetella bronchiseptica | 0.6 | 0.6 |
| Pseudomonas aeruginosa | 80.0 | 80.0 |

Antibiotic RIT D-2214 exhibits in vivo activity against Gram-positive and Gram-negative microorganisms and, hence, is usefull in controlling infections caused by such organisms in host animals. However, the efficacy of antibiotic RIT D-2214 is less advantageous when administered orally.

The level at which monoammonium salt of antibiotic RIT D-2214 shows 50% mice protection against infections with illustrative microorganisms are set forth in Table 2. Comparative trials with ampicillin were performed in vivo according to the usual mice protection test procedure. The test compound was administered in graded dilutions to mice either subcutaneously (s.c.) in water or orally (or.) in combination with calcium carbonate one hour after intravenous infection with uniformly lethal doses of the test organism. The animals were observed for 3 days. The total dose required to protect 50% of the infected mice is designated as the $ED_{50}$, the most potent compound having the lowest $ED_{50}$'s.

TABLE 2

| Test organism | | Administration | RIT D-2214 | Ampicillin |
|---|---|---|---|---|
| Staphylococcus aureus | 663 | s.c. | <11.0 | <11.0 |
| Escherichia coli | 47 | s.c. | <10.0 | 23.6 |
| Escherichia coli | 9 | s.c. | 10.9 | 11.5 |
| Salmonella brandebourg | 22 | s.c. | 13.0 | 36.4 |
| Salmonella enteritidis | 24 | s.c. | 13.5 | 55.6 |
| Salmonella panama | 20 | s.c. | <10.0 | 22.0 |
| Shigella flexneri | 25 | s.c. | 52.5 | >100.0 |
| Proteus mirabilis | 11 | s.c. | <10.0 | 14.8 |
| Klebsiella pneumoniae SK&F 4200 | | s.c. | <11.0 | 36.7 |
| Klebsiella pneumoniae SK&F 4200 | | or. | 25.3 | 50.4 |

TABLE 2-continued

| Test organism | Administration | RIT D-2214 | Ampicillin |
|---|---|---|---|
| Vibrio parahaemoliticus | 194 | or. | 22.7 | 17.9 |

Antibiotic RIT D-2214 exhibits valuable plasma levels when given subcutaneously to mice, rats and dogs, at a single dose of 20 mg/kg. Comparative results with ampicillin are given in Table 3.

Plasma samples were adequately diluted with sterile water and assayed according to the usual agar diffusion method, using Bacillus subtilis ATCC 6633 as the test organism.

Table 3

| | | Plasma levels after minutes (in mcg/ml.) | | | | |
|---|---|---|---|---|---|---|
| | | 5 | 15 | 30 | 60 | 120 |
| Mice | RIT D-2214 | 13 | 15 | 10 | 6.0 | — |
| | ampicillin | 6.5 | 9.0 | 3.5 | 1.0 | — |
| Rats | RIT D-2214 | 12 | 23 | 17 | 12 | 7.5 |
| | ampicillin | 7.0 | 13 | 12.5 | 5 | 2.5 |
| Dog | RIT D-2214 | — | 18 | 23 | 22.5 | 9 |
| | ampicillin | — | 13 | 18 | 18 | 9 |

The monoammonium salt of antibiotic RIT D-2214 does not show any detectable toxicity when administered to mice in a acute toxicity trial, at the relatively high level of 500 mg/kg by intravenous route and 1,000 mg/kg by oral route.

The product of this invention may be administered by parenteral or oral route, being therefore formulated into adequate compositions in the same manner as other penicillin antibacterials. The dose that is administered to the subject will depend on the severity and type of infection as well as the general condition of the subject The following examples are presented to illustrate the invention further; they are not to be construed as limiting the scope thereof.

EXAMPLE 1

A sporulated culture of *Acremonium chrysogenum* ATCC 20.389 is produced by growing the organism on a nutrient agar slant (soybean meal 20 g; calcium carbonate 5 g; glucose 10 g; sucrose 36 g; agar 20 g; one ml. of a 50% L-lysine aqueous solution; deionized water 1 liter) adjusted to pH 7 with phosphoric acid and sterilized for 25 min. at 121° C.

The agar slant is inoculated with spores of *Acremonium chrysogenum* ATCC 20 389 and is incubated for 9 days at 25° C. The agar slant is then covered with 5 to 10 ml. distilled water and gently scraped to removed the spores as an aqueous suspension thereof.

Five ml. of the resulting suspension is used to inoculate 6 liters Erlenmeyer's flasks containing 500 ml. of sterile vegetative medium: (corn steep liquid 10 g; soybean meal 30 g: calcium carbonate 5 g; glucose 20 g; sucrose 20 g; lysine (50% in water) 1 ml.; deionized water 1 liter) adjusted to pH 7 with phosphoric acid and sterilized for 35 min. at 121° C.

The vegetative flasks are shaken for 3 days at 28° C, on a rotary shaker operating with a 50 mm orbit diameter at 150 rpm. The inoculum so prepared is then utilized in the production of antibiotic RIT D-2214 as follows: into a 20 liter laboratory fermentation tank are added 15 liters of a production medium: (soybean meal 300 g; dried distiller solubles 75 g; calcium carbonate 90 g; glucose 300 g; saccharose 525 g; L-lysine (50% in water) 30 ml,; L-carboxymethyl-cysteine 30 g; DL-methionine 60 g; SAG 471 3 ml.; antifoam A 2 ml,; tap water for 14.5 liters) at pH 6.5.

After 30 min. sterilization at 121° C, the tank is incubated with 500 ml. vegetative inoculum.

The fermentation is carried out for 4 days at 25° C, aerated with sterile air at a air flow rate in the range of 0.5 to 1.0 volume per volume of broth per minute, agitated by a mechanical stirrer equipped with 2 flat blade turbines of 13 cm diameter or 0.48 tank diameter, operating from 300 to 450 rpm.

The production of RIT D-2214 is controlled during the fermentation by sampling at regular intervals and assaying for its antibiotic activity after adequate dilution, by the classical agar diffusion method using *Alcaligenes viscolactis* as specific test organism.

Oxygen level and pH are continuously recorded during the fermentation in order to adequately adjust such operating variables as air flow rate, air counter-pressure and agitation speed, according to the art. The fermentation is stopped after a 4 days period, when glucose and sucrose are completely exhausted and the fermentation broth is then supplemented with 0.1% formaldehyde and cooled at 4° C.

Approximately 12 liters of fermentation broth obtained hereinabove are adjusted to pH 3.5 with phosphoric acid and filtered. The 10 liters broth filtrate is thoroughly mixed for 45 min. with 300 g activated carbon (NORIT D — sold by Norit Sales Corporation Ltd. - Amsterdam, The Netherlands), the pH being adjusted to 2.5 with hydrochloric acid. The charcoal is filtered off on Dicalite (a diatomaceous earth sold by Johns-Manville Products Co, New York, USA), washed with water up to decoloration of the effluent and then eluted with a 60:40 acetone/water mixture.

The eluate is concentrated under reduced pressure to remove acetone and poured at a flow rate of 500 ml./h onto a 8 × 42 cm column packed with IRA-402 resin (formate cycle) (an anoin exchange resin sold by Rohm & Haas Co, Philadelphia, USA) and subsequently washed with formic acid to convert it to the formate cycle and with deionized water to reach neutral pH.

The column is washed with water until the effluent is clear and colorless and the antibiotic removed by eluting with 7.5 liters of a 0.2 M ammonium formate solution, at a flow rate of 1 l./h. The antibiotically active fractions (3.6 l.) are combined and concentrated under reduced pressure to approximately 140 ml.

The concentrate is then passed at a rate of 100 ml./h over a 4 × 60 cm column packed with XAD-2 resin (a macroreticular nonionic polymer sold by Rohm & Haas Co. Philadelphia, U.S.A. and previously washed with deionized water up to neutral pH and low conductivity level). The antibiotic is fixed and eluted with deionized water at a rate of 200 ml./h. The most active fractions are combined and concentrated under reduced pressure by azeotropic distillation with isopropanol. The crude product is recovered as a yellow powder by treating the syrupy concentrate with hot ethanol, evaporating the solvent under reduced pressure and washing the precipitate with ether to yield crude monoammonium salt of RIT D-2214.

EXAMPLE 2

Five hundred milligrams aliquot of the crude antibiotic RIT D-2214 obtained at the end of example 1, are dissolved in 2 ml. of deionized water and the solution is poured onto a 1.0 × 30 cm column packed with XAD 4 resin (a nonionic macroreticular polymer sold by Rohm & Haas Co. Philadelphia, U.S.A.) and previously washed with deionized water up to neutral pH and low conductivity level. The antibiotic RIT D-2214 is eluted by washing the column with deionized water. The most active fractions are combined and concentrated under reduced pressure by azeotropic distillation with isopropanol. The monoammonium salt of antibotic RIT D-2214 is obtained as a white powder by treating the syrupy concentrate with hot ethanol, filtering and washing the precipitate with ether.

EXAMPLE 3

Approximately 12 liters of fermentation broth, obtained according to the procedure described in the first part of example 1, are supplemented with 0.1% formaldehyde and filtered on Dicalite (a diatomaceous earth sold by Johns Manville Products Co.) The filtrate (10 l.) is adjusted to pH 5 with phosphoric acid and passed over a 4 × 7.5 cm column of IR 45 ($OH^-$) resin (a weakly basic anion exchange resin sold by Rohm % Haas Co, Philadelphia, U.S.A.), subsequently washed with N sodium hydroxyde to convert the resin to the basic form and with deionized waqter until pH is below 9.0, at a flow rate of 4 l./h. The percolate is acidified to pH 2.5 by slow addition of IR 124 ($H^+$) resin (a strongly acid cationic exchange resin sold by Rohm % Haas Co, Philadelphia, U.S.A.), subsequently washed with N sulfuric acid to convert it to the acid form and with deionized water until pH is above 4 and poured through a 5 × 35 cm column packed with IRA 68 resin (formate cycle, as in example 1), at a rate of 500 ml./h. The column is washed with deionized water until the effluent is clear and colorless and the antibiotic is eluted with 3.5 l. 0.2 M ammonium formate, at 1 l./h. The antibiotically most active fractions (1 l.) are collected and concentrated under reduced pressure to approximately 100 ml. and poured onto a 4 × 40 cm column packed with XAD 2 resin prepared as indicated in example 1. The elution is performed by washing with 200 ml./h deionized water.

Crude ammonium salt of antibiotic RIT D-2214 is recovered from the most active fraction of the eluate according to the isolation procedure described in example 1.

EXAMPLE 4

A 1 g aliquot of crude ammonium salt of antibiotic RIT D-2214 obtained at the end of example 3 is dissolved in 2.5 ml. of water and 5 ml. of isopropyl alcohol is added thereto with stirring. The solution is poured in a polyamide cylinder (4.5 × 50 cm) packed with microcrystalline cellulose and thereafter developped with a 70:30 mixture of isopropyl alcohol and water. The column is then sliced (according to the dry-column chromatography method described by B. Loev and M. M. Goodman in Progress Separation Purification vol. 3, p. 73–95, 1970) in 5 cm thick segments which are poured in sintered glass funnels and triturated with a 50 ml. portion of water and the slices are checked for presence of antibiotic by microbiological testing using *Alcaligenes viscolactis* as test organism.

The pooled solution is treated by azeotropic distillation in the presence of isopropyl alcohol to yield a concentrated solution from which crystallization occurs at 4° C. The precipitate is filtered, washed with cold ethanol and dried over phosphorous pentoxide for 3 days at 25° C under reduced pressure to yield the ammonium salt of antibiotic RIT D-2214 as a white, solid, decomposing at about 142° C, very soluble in water, slightly soluble in methanol and insoluble in other organic solvents.

| Analysis | | calculated (%) | found (%) |
|---|---|---|---|
| ($C_{13}H_{22}N_4O_6S_2$) | C | 39.58 | 39.52 |
| | H | 5.62 | 5.65 |
| | N | 14.20 | 14.26 |

The D configuration of antibiotic RIT D-2214 was demonstrated by determination of the D-configuration of its carboxymethylcysteine fragment. Therefore, the ammonium salt of antibiotic RIT D-2214 was hydrolyzed in normal hydrochloric acid for 8 hrs. at 100° C under nitrogen atmosphere and the obtained carboxymethylcysteine was isolated by column chromatography on strong basic anionic resin. The mixed melting point between this product and D-carboxymethylcysteine obtained by chemical synthesis is 185°–186° C, i.e. identical to the melting point of the chemically synthesized product, the melting point of the chemically synthesized L-carboxymethylcysteine being 195°–196° C.

The infrared absorption spectrum of the monoammonium salt of antibiotic RIT D-2214 in 1% potassium bromide presents distinguishable bands in the infrared spectrum over the range of 1,000 to 4,000 $cm^{-1}$ as follows: 3,400 (broad band); 2,950; 1,770; 1,650-1,600 (broad band); 1,540 (shoulder); 1,410; 1,330; 1,120.

The NMR spectrum of antibiotic RIT D-2214 at 15% in $D_2O$, with tetramethyl silane as reference, shows the following characteristics: 8.4 ppm(d); 6.85 ppm(t); 6.6 ppm(s); 6.1 ppm (q); 5.85 ppm(s); 4.5 ppm(q).

Paper chromatography on Whatman N° 4 paper of the monoammonium salt of antibiotic RIT D-2214 gives the following Rf values in two different solvent systems (comparison made with ampicillin).

| Solvent system (upper phase) | Ant. RIT D-2214 | Ampicillin |
|---|---|---|
| n-Butanol, ethanol, water (4:1:5) | 0.18 | 0.43 |
| n-Butanol, acetic acid, water (4:1:5) | 0.43 | 0.69 |

Bioautographs were obtained by placing the paper chromatograph on agar plates seeded with sensitive organisms, such as *Alcaligenes viscolactis* and *Bacillus subtilis* ATCC 6633 as test organisms.

When subjected to thin layer chromatography (TLC) on silicagel plates (TCL — ready plastic sheets F1500 LS 254 — silica gel from Schleicher & Schull, Dassel, W. Germany) carried out with the following solvent systems and tested with ninhydrin spray reagent as a detector, the monoammonium salt of antibiotic RIT D-2214 shows the following Rf values:

n-butanol, ethanol, acetic acid, water (10:1.5:1.5:2) — 0.72
n-butanol, acetic acid, water (4:1:1) — 0.63
acetonitrile, water (75:25) — 0.22

Antibiotic RIT D-2214 shows a positive test with ninhydrin, sodium hydroxyde-iodine, sodium azide and chloroplatinic acid. Antibiotic RIT D-2214 can be colorimetrically assayed by the classical hydroxylamine method of penicillin assay. Antibiotic RI D-2214 is relatively stable under acid conditions. Comparative trials were performed with the monoammonium salt of antibiotic RIT D-2214, penicillin G and ampicillin, in reconstituted gastric juice, at pH 1.3. Recoveries were estimated according to the hydroxylamine assay method. The corresponding half-life, expressed in minutes, are respectively 7 for penicillin G, 25 for antibiotic RIT D-2214 and 390 for ampicillin. Antibiotic RIT D-2214 is relatively stable when kept at 4° C in a water solution for not more than 7 days.

Antibiotic RIT D-2214 is rapidly destroyed by a Staphylococcal preparation of $\beta$-lactamase (Penase Leo from Leo pharmaceuticals products, Ballerup, Danemark).

EXAMPLE 5

Twelve liters of fermentation broth obtained according to the procedure described in the first part of Example 1 are extracted according to the procedure of Example 3, but the elution of the IRA-68 resin is performed with 3.5 l. of 0.2 M sodium acetate. The most active fractions are collected and treated as described in Example 3 to yield sodium salt of antibiotic RIT D-2214.

EXAMPLE 6

A sporulated culture of *Acremonium chrysogenum* ATCC 20 389 is produced by growing the organism on a nutrient agar slant (soybean meal 20 g; calcium carbonate 5 g; glucose 10 g; sucrose 36 g; one ml. of 50% L-lysine aqueous solution; agar 20 g; deionized water 1 liter) adjusted to pH 7 with phosphoric acid and sterilized for 25 min. at 121° C.

The agar slant is inoculated with spores of *Acremonium chrysogenum* ATCC 20 389 and is incubated for 9 days at 25° C. The agar slant is then covered with 5 to 10 ml. distilled water and gently scraped to remove the spores as an aqueous suspension thereof.

One ml. of the resulting suspension is used to inoculate 250 ml. Erlenmeyer's flasks containing 50 ml. of sterile vegetative medium: (corn steep liquid 10 g; soybean meal 30 g; calcium carbonate 5 g; glucose 20 g; sucrose 20 g; 1 ml. of 50% L-lysine aqueous solution; deionized water 1 liter) adjusted to pH 7 with phosphoric acid and sterilized for 35 min. at 121° C.

The vegetative flasks are shaken for 3 days at 28° C, on a rotary shaker operating with a 50 mm orbit diameter at 260 rpm. This inoculum is then used in the production of antibiotic RIT D-2214 A production medium consisting of: soybean meal 15g; calcium carbonate 5g; glucose 10 g; saccharose 36 g; DL-methionine 1 g; L-lysine (50% in water) 1 ml.; L-carboxymethylcysteine 0.5 g; deionized water 1 liter, adjusted to pH 7 with phosphoric acid and distributed in 250 ml. Erlenmeyer's flasks with 30 ml. medium content and sterilized for 35 min. at 121° C is inoculated with 5% vegetative inoculum and incubated at 25° C for 5 days on a rotary shaker operating with a 50 mm orbit diameter at 260 rmp.

The production of antibiotic RIT D-2214 is controlled during the fermentation by sampling at regular intervals and assaying for its antibiotic activity after adequate dilution by a classical agar diffusion method using *Alcaligenes viscolactis* as specific test organism.

EXAMPLE 7

Using the technique of example 6 but replacing the therein described production medium by a production medium having the following composition: (soybean meal 15 g; dried distiller solubles 5 g; glucose 10 g; molasses 20 g; DL-methionine 2 g; L-lysine (50% in water) 1 ml.; L-carboxymethylcysteine 0.5 g; deionized water 1 liter) adjusted to pH 7 with phosphoric acid, crude antibiotic RIT D-2214 is obtained.

EXAMPLE 8

Using the technique of example 6. but replacing the therein described production medium by a production medium having the following composition: herring meal 20 g; calcium carbonate 3 g; glucose 10 g; saccharose 40 g; oleic acid 5 ml.; D-L methionine 1 g; one ml. of 50% L-lysine aqueous solution; L-carboxymethylcysteine 0.5 g; deionized water 1 liter) adjusted to pH 7 with phosphoric acid, crude antibiotic RIT D-2214 is obtained.

EXAMPLE 9

To a solution of 3.63 g (0.03 mole) of D-cysteine and 2.4 g (0.03 mole) of ammonium bicarbonate in 100 ml. of water flushed with nitrogen, there is added, at once, with vigorous stirring 11.25 g (0.03 mole) of 6-($\alpha$-bromoacetamido)-penicillanic acid ammonium salt (prepared according to Y. G. Perron, W. F. Minor et al., in J. Amer. Chem. Soc. 82, 3934-8, 1960).

The mixture is stirred at room temperature for about 30 minutes, then rapidly cooled to 5° C, layered with 3 × 100 ml. of methyl isobutylketone (MIBK) and extracted by mixing vigorously while adjusting the pH to 3 with DOWEX -50×12($H^+$)(a product of Dow Chem. Co, Midland, Michigan, USA).

The combined MIBK extracts are eliminated and the aqueous phase is concentrated up to 20 ml. by evaporation under reduced pressure at 30° C, the pH being adjusted to 7 by the addition of a few drops of 25% ammonium hydroxide solution. The residue is taken up in 500 ml. ice-cold ethanol, stirred for 20 minutes and the thus obtained precipitate is filtered, washed with 10 ml. cold ethanol and 50 ml. diethyl ether and dried over $P_2O_5$ under reduced pressure to yield the crude ammonium salt of antibiotic RIT D-2214.

EXAMPLE 10

Two grams of crude ammonium salt of antibiotic RIT D-2214 obtained at the end of example 9 are dissolved in 5 ml. of water and poured in a column (4×75 cm) packed with 628 ml. of XAD-4 resin in water. The column is eluted with water, each 25 ml. fraction collected being checked up for antibiotic content by conductivity and thin-layer chromatography.

The so-obtained fractions are combined, treated in the same as in the beginning of example 4 and freeze-dried to yield pure ammonium salt of antibiotic RIT D-2214 showing the same physico-chemical characteristics as those described at the end of example 4.

EXAMPLE 11

Using the procedure described in the example 9 but replacing D-cysteine by L-cysteine, crude ammonium salt of antibiotic RIT L-2214 is obtained. This crude product is purified as indicated in the example 10.

The following Table 4 shows that the monoammonium salt of antibiotic RIT L-2214 also is active against Grampositive and negative bacteria, but less than the monoammonium salt of RIT D-2214.

TABLE 4

| Test organism | Minimum inhibitory concentration (in mcg/ml.) | |
|---|---|---|
| | Antib. RIT L-2214 | Ampicillin |
| Staphylococcus aureus | 1.25 | 1.25 |
| Staphylococcus aureus Pen. res. | 80.0 | 20.0 |
| Escherichia coli | 40.0 | 1.25 |
| Escherichia coli Pen. resistant | 80.0 | 80.0 |
| Aerobacter aerogenes | 20.0 | 1.25 |
| Klebsiella pneumoniae | 80.0 | 40.0 |
| Salmonella paratyphi | 20.0 | 1.25 |
| Shigella sonnei | 80.0 | 2.5 |
| Proteus mirabilis | 20.0 | 1.25 |
| Proteus morganii | 80.0 | 20.0 |
| Pseudomonas aeruginosa | 80.0 | 80.0 |
| Bacillus subtilis | 0.31 | 0.3 |

EXAMPLE 12

Using the procedure described in example 9 but replacing D-cysteine by DL-cysteine, crude ammonium salt of antibiotic RIT DL-2214 is obtained. This crude product is purified as indicated in the example 10.

The activity of this compound against Gram-positive and negative bacteria has approximately half the value of that shown by the RIT L-2214.

EXAMPLE 13

Using the procedure described in example 9 but replacing 6-(α-bromoacetamido)-penicillanic acid ammonium salt by 6-(α-bromoacetamido)-penicillanic acid sodium salt (prepared according to Y. G. Perron, W. F. Minor et al. in J. Amer. Chem. Soc. 82, 3934-8, 1960), crude sodium salt of antibiotic RIT D-2214 is obtained. This crude product is purified as indicated in example 10.

EXAMPLE 14

An injectable pharmaceutical composition is formed by adding sterile water or sterile saline solution (2 ml.) to 500 mg of RIT D-2214 (monoammonium salt).

EXAMPLE 15

An antibacterial capsule has the following components: RIT D-2214 (monosodium salt) 500 mg; calcium carbonate 250 mg; magnesium stearate 75 mg.

We claim:
1. A method of producing the compound 6-[(D)-(2-amino-2-carboxyethylthio)acetamido]penicillanic acid of the formula

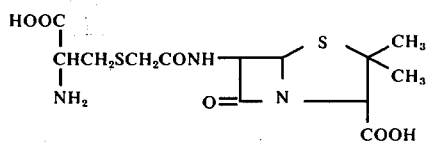

which comprises cultivating Acremonium chrysogenum ATCC 20,389 in a culture medium containing assimilable sources of carbon and nitrogen, inorganic salts, L-lysine, and L-carboxymethylcysteine under submerged aerobic conditions until a substantial amount of the said compound is produced.

2. A method according to claim 1, wherein the culture medium contains L (+) lysine and is maintained at a temperature of from approximately 20° C to approximately 37° C and the growth of the organism is carried out for a period of approximately 36 to 96 hours.

3. A method according to claim 2 additionally comprising recovering the said compound from said culture medium.

* * * * *